US007879199B2

(12) United States Patent
Gharda et al.

(10) Patent No.: US 7,879,199 B2
(45) Date of Patent: Feb. 1, 2011

(54) POLYETHER KETONE, ITS MONOMER AND ITS PHENOLATE

(75) Inventors: Keki Hormusji Gharda, Mumbai (IN); Ashokkumar M. Malte, Thane (IN); Suchet S. Mathur, Dombivli (IN); Pulinattu C. Joseph, Thane (IN); Mathew Abraham, Navi Mumbai (IN); Janardan K. Nambodari, Dombivli (IN); Sanjay C. Limaye, Kalyan (IN); Shekhar V. Sathe, Dombivli (IN); Kailas Ambadas Chavan, Dombivli (IN); Deepak R. Naladkar, Badlapur (IN)

(73) Assignee: Gharda Chemicals Limited, Maharashtra (IN)

( * ) Notice: Subject to any disclaimer, the term of this patent is extended or adjusted under 35 U.S.C. 154(b) by 250 days.

(21) Appl. No.: 12/150,511

(22) Filed: Apr. 29, 2008

(65) Prior Publication Data

US 2009/0240020 A1 Sep. 24, 2009

(30) Foreign Application Priority Data

Mar. 24, 2008 (IN) .................. 571/MUM/2008

(51) Int. Cl.
*B01D 3/34* (2006.01)
*C07C 45/00* (2006.01)
*C07C 49/00* (2006.01)
(52) U.S. Cl. .................. 203/57; 203/62; 568/324; 568/337
(58) Field of Classification Search .............. 528/126; 568/324, 337; 203/57, 62
See application file for complete search history.

(56) References Cited

U.S. PATENT DOCUMENTS

| 2,284,124 | A | * | 5/1942 | Britton et al. ............. 203/48 |
| 3,403,183 | A | * | 9/1968 | Dobratz et al. ............ 568/324 |
| 3,819,492 | A | * | 6/1974 | Stevenson et al. .......... 203/34 |
| 3,850,988 | A | * | 11/1974 | Ruby ..................... 568/324 |
| 3,953,400 | A | * | 4/1976 | Dahl ..................... 528/179 |
| 4,599,452 | A | * | 7/1986 | Colquhoun et al. ......... 568/319 |
| 4,604,485 | A | * | 8/1986 | Colquhoun ............... 568/319 |
| 4,612,399 | A | * | 9/1986 | Colquhoun et al. ......... 568/324 |
| 4,707,536 | A | * | 11/1987 | Yoneda et al. ............ 528/198 |
| 4,711,945 | A |   | 12/1987 | Daniels |
| 4,950,729 | A | * | 8/1990 | Daniels .................. 528/86 |
| 4,952,665 | A |   | 8/1990 | Ebata et al. |
| 5,137,988 | A | * | 8/1992 | Matzner et al. ........... 525/471 |
| 5,147,512 | A | * | 9/1992 | Berg et al. ............... 203/51 |
| 5,171,821 | A | * | 12/1992 | Nozawa et al. ............ 528/125 |
| 5,290,906 | A | * | 3/1994 | Matsumura et al. ......... 528/125 |
| 5,326,849 | A | * | 7/1994 | Takahashi et al. .......... 528/207 |
| 5,523,384 | A | * | 6/1996 | Memeger et al. ........... 528/392 |
| 2002/0040124 | A1 | * | 4/2002 | Gharda et al. ............. 528/486 |
| 2003/0176635 | A1 | * | 9/2003 | Gharda et al. ............. 528/486 |
| 2005/0183942 | A1 | * | 8/2005 | Blaschke ................. 203/6 |
| 2006/0054486 | A1 | * | 3/2006 | Clark .................... 203/59 |
| 2008/0085990 | A1 | * | 4/2008 | Richter et al. ............ 528/126 |
| 2009/0240020 | A1 | * | 9/2009 | Gharda et al. ............. 528/126 |

FOREIGN PATENT DOCUMENTS

| EP | 0 154 092 | 9/1985 |
| EP | 0 344 688 | 12/1989 |
| EP | 1 903 024 | 3/2008 |
| JP | 03-041047 | 2/1991 |
| JP | 5-178983 | 7/1993 |
| JP | 5-178984 | 7/1993 |

OTHER PUBLICATIONS

Perry's Chemical Engineers' Handbook (Distillation, 7th Edition, 1997, p. 13-1-13-108).*
Fair (Distillation, Kirk-Othmer Encyclopedia of Chemical Technology, 2001).*
Machine translation of JP 05178984 2009.*
European Search Report of EP 1 903 024 dated Jan. 21, 2008.
Attwood, T. E. et a;, "Synthesis and properties of polyaryletherketones," Polymer, 1981, vol. 22, pp. 1096-1103. (Spec, pp. 2 and 16) (European Search Report).
Fukawa et al., "Preparation of Aromatic Poly(ether ketones) from an Aromatic Dihalide and Sodium Carbonate," Macromolecules, 1991, vol. 24, pp. 3838-3844. (Spec, p. 3).
R. Bruce Prime, "Thermo-Oxidative Decomposition of Poly (Ether Ether Ketone)," Journal of Polymer Science, Part C: Polymer Letters, 1986, vol. 24, pp. 641-644. (Spec, p. 3).
Jin et al., "*A facile method for preparation of high-purity 4-hydroxy-4'-chlorobenzophenone*," Chemical Abstracts Service, Columbus, Ohio, retrieved from STN Database accession No. 2001:460231. & Zhejiang Gongye Daxue Xuebao, 28 (2); 138-141 Coden: ZDXUF2; ISSN: 1006-4304, 2000. XP-002465390 (European Search Report).

* cited by examiner

*Primary Examiner*—Mark Eashoo
*Assistant Examiner*—Liam J Heincer
(74) *Attorney, Agent, or Firm*—Collard & Roe, P.C.

(57) ABSTRACT

A process for the preparation of an alkali metal salt of 4-chloro-4'-hydroxy benzophenone including the steps of (a) preparing purified 4-chloro-4'-hydroxy benzophenone by a process including distilling under reduced pressure a liquid containing 4-chloro-4'-hydroxy benzophenone and a solvent selected from diphenyl sulphone, diphenylene sulphone, benzophenone and dichlorobenzophenone, and then (b) preparing the alkali metal salt of thus purified 4-chloro-4'-hydroxy benzophenone by the reaction of the purified 4-chloro-4'-hydroxy benzophenone with a stoichiometric excess of at least one alkali metal base. There is also described a polymerization process using the alkali metal salt to yield PEK with high inherent viscosity and improved mechanical and thermal properties.

23 Claims, No Drawings

POLYETHER KETONE, ITS MONOMER AND ITS PHENOLATE

CROSS REFERENCE TO RELATED APPLICATIONS

Applicants claim priority under 35 U.S.C. §119 of Indian Application No. 571/MUM/2008 filed Mar. 24, 2008.

The present invention relates to polyether ketones, their monomers and their phenolates.

PRIOR ART

Linear unsubstituted polyether ketone (PEK) and polyether ether ketone (PEEK) are crystalline aromatic super heat resistant thermoplastic resins. They are highly functional engineering plastics having properties far exceeding those of the thermoplastic resins of the past, and they possess excellent processing properties along with other unique properties not found in other plastics. These polymers find special applications in automotive, aerospace and engineering components which experience or continually operate at very high temperatures. These include automotive, under the bonnet parts, headlamp reflectors, aircraft exterior and in aircraft components, wire and cable insulation, industrial valve linings and heat exchanger parts.

Though PEK and PEEK are similar in structure and properties, PEK possesses further superior heat resistance and chemical resistance as well as higher mechanical properties than PEEK.

In spite of its superior properties, commercial use PEK has so far been limited due to limited availability and high price as compared to PEEK. Hence the need for an economic route to PEK remained a necessity and it is this objective and motivation which have driven our research towards it.

Though several routes have been published in the literature on the synthesis of PEK, our research has shown that these are not economically feasible manufacturing processes. The routes of manufacturing PEK can be broadly classified into electrophilic route and nucleophilic route. The electrophilic route uses highly corrosive protonic acid or Lewis acid, and the reaction selectivity is also not sufficient to obtain predominantly para substitution and it has the problem of low thermal stability of the polymer obtained by the generation of ortho substituted material.

Using the nucleophilic route, a polymer having a high degree of polymerization can be obtained. For example Polymer 1981, Vol 22, page 1096 describes the preparation of PEK by reaction of 4,4'-difluoro diphenyl ketone and the potassium salt of 4,4'-dihydroxydiphenyl ketone in diphenyl sulphone solvent at 335° C. This route employs the expensive dihydroxy compound as well as the additionally expensive difluoro compound. Due to the low solubility of the dipotassium salt of 4,4'-dihydroxydiphenyl ketone in $DPSO_2$ solvent the reaction rate is limited. Also the carbonyl group further reduces the nucleophilic reactivity of dipotassium salt of 4,4'-dihydroxydiphenyl ketone.

The above reference also describes polymerization using a single monomer, namely the potassium salt of 4-fluoro-4'-hydroxy diphenyl ketone. However the authors have observed branching in the polymer made by this route due to abstraction of protons ortho to the aromatic fluorine and the generation of carbanions.

Macromolecules, 1991, Vol. 24, page 3838 describes the preparation of PEK from 4,4'-dichlorobenzophenone and sodium carbonate in the presence of fumed silica and catalysed by copper. While using cheap raw materials, this route is not commercially practiced possibly due to the presence of extra non-reactants/catalysts which are difficult to remove during the subsequent workup.

To overcome the problem of costs associated with the production of PEK by reaction of difluorobenzophenone and dihydroxybenzophenone, U.S. Pat. No. 4,711,945 describes the use of 4-chloro-4'-hydroxybenzophenone. However the inventors "have experienced problems in consistently obtaining a polymer of satisfactory properties while using this monomer". Hence they have suggested the use of a copper compound to accelerate the reaction and obtain polymer of high molecular weight. However the presence of copper in trace amounts in the final polymer is known to accelerate degradation of the polymer during processing at high temperatures (Journal of Polymer Science, Part C: Polymer Letters, Vol. 24, 641-644 (1986)) and its complete removal from the polymer presents difficulties.

Japanese unexamined patent Application H5-178983 describes the use of sodium sulphate at levels of 15 wt. % concentration during the polymerization reaction of 4-chloro-4'-hydroxybenzophenone to obtain an inherent viscosity (IV) of 0.92 dl/g. However this is an additional reactant which has to be removed during processing.

Japanese unexamined patent Application JP 5178984 describes the use of potassium phosphate in 1-3 mole % molar ratio to minimize branching during polymerization of 4-chloro-4'-hydroxybenzophenone. However the maximum inherent viscosity they obtained was 0.74 dl/g.

EP 344688 teaches the polymerization of 4-chloro-4'-hydroxybenzophenone without the use of any catalyst/non-reactant. The preferred base is potassium hydroxide. However the reaction times are long, 12-14 hours at 320° C., and the maximum inherent viscosity obtained is 0.88 dl/g. It is known that prolonged heating of the polymerization reaction mass at temperatures in excess of 300° C. leads to side reactions.

In view of all of the above the need was clearly felt for a process using 4-chloro-4'-hydroxybenzophenone as the monomer which does not use any additive to accelerate the polymerization rate, and wherein polymerization can be completed in 1-3 hours at temperatures in the range of 300-320° C. Also the inherent viscosity of the polymer obtained should be >0.9 dl/g.

SUMMARY OF THE INVENTION

It was to achieve these aims that an earnest work was undertaken. As a result the present inventors have found that the reason for the slow polymerization of 4-chloro-4'-hydroxybenzophenone is the presence of impurities in 4-chloro-4'-hydroxybenzophenone which are difficult to remove by conventional solvent crystallization unless a large number of crystallizations are carried out, thus making the process uneconomical. In order to overcome this the present inventors have discovered a method of purifying the monomer by direct distillation or more elegantly by the co-distillation of the monomer with a compatible solvent such as diphenyl sulphone.

Having overcome the problem of obtaining a monomer of the required purity, the present inventors have further concentrated their efforts on the method of polymerizing the said purified monomer.

As a result of exhaustive research work in this area, we have now found that it is possible to produce a polymer, polyether ketone, meeting all the required specifications by a process described hereunder, by which process the polymerization can be effected at a temperature of 300-320° C., the polymerization can be completed in 1-3 hrs and an inherent viscosity >0.9 dl/g, and even an inherent viscosity >1.0 dl/g, is readily obtainable.

During our research we have discovered that the rate of the polymerization reaction of 4-chloro-4'-hydroxybenzophenone is very much dependent on the method of preparing the alkali metal salt of 4-chloro-4'-hydroxybenzophenone. In addition it has been discovered that the properties of the polymer are also dependent on the method of preparing the alkali metal salt of the polymer 4-chloro-4'-hydroxy-benzophenone.

As a result of our work we have also found that it is preferable to maintain the pH of the polymerization reaction mass in the alkaline range of 9-11. If the pH is maintained in this range the polymerization proceeds smoothly and the subsequent end capping is also efficient. However if the pH drops to below 9, then the polymerization becomes sluggish, and the endcapping of the polymer is not efficient and leads to poor thermal stability of the resultant polymer. To maintain the pH between 9-11 at least one appropriate buffering agent should be added.

It is also surprisingly found that by the method of the invention described hereunder it is possible to conduct the continuous polymerization of 4-chloro 4'-hydroxy benzophenone. Using this method of continuous polymerization, the production of very large quantities of the hitherto scarce and expensive polymer are now made practically possible, thus further bringing down the cost of the product substantially and making it available in large quantities for commercial usage. The invention will now be described in detail.

DESCRIPTION OF THE INVENTION

The present invention relates to improved processes for purifying a monomer, to producing a suitable phenolate from it and to processes for its polymerization to polyether ketone.

The present invention provides processes for purifying the monomer, 4-chloro,4'-hydroxy benzophenone (I), often referred to simply as CHBP, whose structural formula is shown at (1) below:

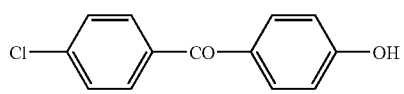
(I)

The present invention also provides both processes for preparing the metal phenolate of CHBP having the formula (II) below:

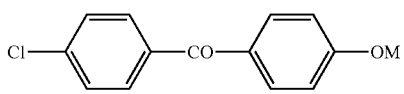
(II)

and processes for producing an aromatic polyether ketone (PEK) of formula (III) below having a high degree of polymerization and having excellent thermal and mechanical properties:

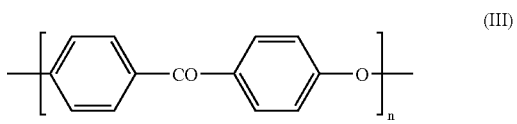
(III)

A) Processes for Purifying the Monomer

As mentioned in the prior art referred to above, the available published literature indicates that the polymerization of the alkali metal salt (II) is sluggish, but we have found that the reason for the slow polymerization of the alkali metal salt of 4-chloro-4'-hydroxybenzophenone (II) is the presence of impurities in the 4-chloro-4'-hydroxybenzophenone (I) which are difficult to remove by conventional solvent crystallization unless a large number of crystallizations are carried out, thus making the process uneconomical.

Our research on this led to the finding that a good way to purify the monomer is by distillation under vacuum, which is hitherto unreported. 4-Chloro-4'-hydroxy benzophenone (CHBP), during its manufacture retains high molecular weight impurities, aluminium salts, etc, which are difficult to remove by normal purification methods. The physical properties of some relevant compounds and mixtures are set out in Table 1 below.

TABLE 1

| Compound | BP. °C. | Pressure mm Hg | M.P. °C. | Thermal stability DSC Method |
|---|---|---|---|---|
| 4-Chloro-4'-hydroxybenzophenone (CHBP) | 213 223 | 1 2 | 182 | Begins to decompose at 240° C. |
| Diphenylsulfone (DPSO₂) | 195 205 | 2.5 4.5 | 129 | Stable up to 378° C. (B.P.) |
| Mixture of CHBP + DPSO₂ (1:2.6) | 192-205° C. | 2.5 | 115-120 | — |

Thermal instability, high melting point and boiling point pose problems in the distillation of CHBP.

However using a short contact distillation technique and special scrape surface condensers, we succeeded in the distillation process. The small difference between the boiling point and the melting point of CHBP made this method of distillation a highly skilled engineering operation. Compared with the monomer formed via the crystallization route, the distilled product gave consistent and superior performance in the polymerization step and better polymer properties.

In order to overcome the difficulties in distillation, attempts were made to co-distill CHBP with other close boiling compounds. Reduced pressure distillation was tried and found effective for compatible solvents which lower the boiling point of CHBP and which are thermally stable at the lowered boiling point. The distillation should be preferably carried out at reduced pressure of less than 5 mmHg, more preferably 3 to 1 mm Hg, and for practical convenience about 2.5 mm Hg. Due to diphenyl sulfone being used as a possible solvent for the polymerization step, this was tried as the compound for co-distillation with CHBP and it was surprisingly found that DPSO₂ is an abundantly suitable compound also for such co-distillation. Moreover diphenyl sulphone is thermally very stable and is a very suitable solvent for the monomer for the polymerization step.

The compound chosen for co-distillation should be one having a boiling point close to that of 4-chloro-4'-hydroxy benzophenone and a lower melting point, and also should be thermally very stable. In addition the solvent chosen for the co-distillation should preferably be such that the co-distilled material can be directly used in the polymerization reaction without having to separate the monomer from the solvent. This means that the solvent should be compatible for subsequent polymerization and that the polymerization using the solvent should produce polymer having the desired properties. The quantity of solvent to be added should be such as to effect the distillation of the monomer 4-chloro-4'-hydroxy benzophenone and also effect the subsequent polymerization step. The quantity of solvent required for either or both distillation and subsequent polymerization should be such as will not affect the economics of the process adversely. Considering all these limitations for a suitable solvent only a few solvent meet all the above mentioned criteria. Compounds other than $DPSO_2$ which are currently commercially available and which can be used are diphenylene sulfone, benzophenone and dichlorobenzophenone. However these others were found not to be as good as diphenyl sulfone for the co-distilling step as well as for the polymerization step.

The melting point of the mixture of 1:2.6 parts by volume of CHBP:$DPSO_2$ which is the optimum composition used for polymerization, dropped to 115° C. This solved the engineering problems associated with the high melting point during distillation of CHBP alone. Our experiments gave results which showed that the mixture of CHBP+$DPSO_2$ distilled at a lower temperature than the individual components (see Table 1 above) and that the distillation proceeded smoothly. This was attributed possibly to an azeotrope formation between CHBP and $DPSO_2$. The generally preferred range for CHBP:co-distilling solvent is 1:2 to 1:5 parts by volume.

Having overcome the problem of obtaining a monomer of the required purity, the present inventors have further concentrated their efforts on the method of polymerizing the said purified monomer.

As a result of exhaustive research work in this area, we have now found that it is possible to produce a polymer, polyether ketone, meeting all the required specifications by a process described hereunder, by which process the polymerization can be effected at a temperature of 300-320° C., the polymerization can be completed in 1-3 hrs and an inherent viscosity >0.9 dl/g, and even an inherent viscosity >1.0 dl/g, is readily obtainable.

During our research we have discovered that the rate of the polymerization reaction of 4-chloro-4'-hydroxybenzophenone is very much dependent on the method of preparing the alkali metal salt of 4-chloro-4'-hydroxybenzophenone. In addition it has been discovered that the properties of the polymer are also dependent on the method of preparing the alkali metal salt of the polymer 4-chloro-4'-hydroxy-benzophenone.

Also as a result of our extensive work we have found that though a polymer of high inherent viscosity >0.9 dl/g and even an inherent viscosity >1.0 dl/g can be produced, the properties of the polymer such as thermal, flow, mechanical, etc. are also dependent on the method of producing the same.

B) Processes for Producing a Suitable Phenolate
A phenolate of the formula

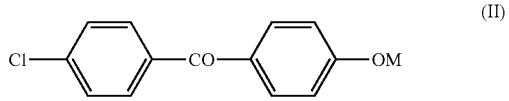

(II)

where M is an alkali metal can be prepared quite easily by the reaction of CHBP(I) with at least one base, or a combination of two bases, with the alkali metal atom being the same or different. As the alkali compound, an hydroxide of an alkali metal, such as sodium hydroxide, potassium hydroxide or lithium hydroxide, a carbonate salt of an alkali metal, such as sodium carbonate or potassium carbonate, or a bicarbonate salt of an alkali metal, such as sodium bicarbonate or potassium bicarbonate, can be used.

The alkali metal hydroxide, carbonate or bicarbonate which is the at least one base is generally used in greater than the stoichiometric proportion with respect to the phenolic groups. More than one base may be used and even a different base, for example an alkali metal carbonate or bicarbonate, may be used to provide the excess of base, if an alkali metal hydroxide has been pre-reacted in a stoichiometric proportion or measured deficiency with CHBP (I).

After extensive research, it has been found surprisingly that contrary to published information where potassium hydroxide is described as the preferred base (EP 344688, JP 5178984, H5-178983), we have obtained consistently good results with sodium hydroxide alone or sodium carbonate alone or a mixture of the two where sodium carbonate is used to provide the excess of base when sodium hydroxide has been pre-reacted in a stoichiometric proportion or measured deficiency with (I). Of the latter the use of sodium carbonate to provide the excess of base when sodium hydroxide has been pre-reacted in a stoichiometric proportion or measured deficiency with (I) is the most preferred method.

We have found that though a PEK having inherent viscosity of >0.9 dl/g and even an inherent viscosity >1.0 dl/g is able to be produced by using potassium as the alkali metal the properties of the polymer such as flow, thermal, mechanical etc are not satisfactory. However when using sodium as the alkali metal not only is a PEK having inherent viscosity of >0.9 dl/g and even an inherent viscosity >1.0 dl/g able to be produced but the properties of the produced polymer are also excellent.

The salt is very easily formed in aqueous or methanolic solution. However since the polymerization is affected by the presence of —OH containing compounds such as water and alcohols it is highly desirable to remove such compounds, including any water which is present as water of crystallization, prior to carrying out the polymerization. The reason why it is important to remove the water completely from the alkali metal salt (II) after its preparation is to prevent the hydrolysis of chlorine, the rate of which increases at higher temperatures, and such hydrolysis upsets the stoichiometric ratio between the chlorine and the phenolate groups and prevents molecular weight buildup. Most of the water can be distilled off from the salt. However to remove the last traces it is often necessary to apply vacuum during the polymerization step.

The alkali metal salt of CHBP can be easily made by the dissolution of CHBP into a solution of the alkali metal hydroxide in a suitable solvent. The suitable solvent can be water or methanol or a 90:10 by volume mixture of methanol and water. The amount of CHBP and the amount of the alkali metal hydroxide used are carefully adjusted so that there is a maximum of 1 mole of hydroxide and more preferably a maximum of 0.99 moles of hydroxide to one mole of CHBP. Excess base is added as the carbonate or bicarbonate. The excess of base is preferably an excess in the range from 1-7% and particularly in the range from 1-5% and especially in the range from 2-3% molar. The mixture of alkali metal hydroxide and carbonate and CHBP in the solvent is stirred until the CHBP has dissolved and then the solvent is evaporated off, for example by simple distillation. Alternatively other methods of removing the solvent and obtaining the alkali metal salt are possible such as by spray drying, passing the solution through an agitated thin film drier, etc. The obtained alkali metal salt of CHBP (II) may be in the hydrated form. The hydrated salt can be dehydrated by heating the salt under vacuum, or also by heating a slurry of the salt and diphenyl sulphone, at a temperature above 150° C., preferably above 200° C., and preferably under a partial vacuum e.g. 25 to 400 torr. After dehydrating the salt by removal of all the water, the temperature can then be increased to the polymerization temperature.

Another method of removal of water from the aqueous solution is by azeotropic distillation with an appropriate organic solvent capable of forming an azeotropic mixture with water. By an appropriate solvent is meant an organic solvent that by forming an azeotropic mixture with water is able to remove all the moisture and which does not affect the subsequent polymerization. Our research has led us to the finding that chlorinated aromatic solvents like chlorobenzene, dichlorobenzene and trichlorobenzene, which are deactivated molecules, are the most suitable solvents and are more effective than activated aromatic solvents such as toluene, xylene, trimethyl benzene and other alkylated aromatics which, though able to remove the moisture, affect the subsequent polymerisation.

C) Processes for its Polymerization to Polyether Ketone

The polymerization reaction is carried out by the method described in detail below in the presence of a suitable solvent and at elevated temperatures. Diphenyl sulphone is the preferred solvent due to its thermal stability as well as its ability to dissolve the polymer PEK at elevated temperatures. The diphenyl sulphone may be added in the range of 400 gm/mole of CHBP to 2000 gms/mole of CHBP. The more preferred range is 500 gms/mole to 1000 gms/mole of CHBP.

The polymerization reaction is preferably carried out at an elevated temperature of from 250-350° C. and more preferably from 280-330° C. As is well known an increase in reaction temperature leads to a shorter reaction time but with the risk of product decomposition and/or side reactions, while a decrease in reaction temperature leads to a longer reaction time but less product decomposition. Hence it is desired to maintain as low a temperature as possible. On the other hand it is important to use a temperature at which the polymeric material is in solution, and in the case of PEK temperatures in excess of 300° C. are required to keep it dissolved in diphenyl sulphone. The solubility of PEK in diphenyl sulphone increases with temperature. Hence the optimum temperature range is 300-330° C. and it is even more preferred to carry out the reaction between 305 and 320° C.

It is also highly desirable to carry out the polymerization essentially in the absence of —OH containing compounds such as water and alcohols. This is to prevent the hydrolysis of chlorine, the rate of which increases at higher temperatures, and such hydrolysis upsets the stoichiometric ratio between the chlorine and the phenate groups and prevents molecular weight buildup. Though most of the water can be distilled off from the salt during its preparation stage, to remove the last traces, it is usually necessary to apply a vacuum during the polymerization step. The hydrated salt can be dehydrated by heating the salt under vacuum, or also by heating a slurry of the salt and diphenyl sulphone at a temperature above 150° C., more preferably above 200° C., preferably under a partial vacuum of e.g. 25 to 400 torr. After dehydrating the salt by removal of preferably all of the water, the temperature can then be increased to the polymerization temperature.

As a result of our research we have found surprisingly that the polymerization rate using the alkali metal salt of CHPB is even faster than that obtainable by the reaction between difluorobenzophenone and the alkali metal salt of dihydroxybenzophenone. This result is totally unexpected since the reactivity of an aryl fluoride is known to be much higher than that of the corresponding aryl chloride for nucleophilic aromatic substitutions. The reason for this higher rate of reaction with the chlorophenoxide is the complete solubility of the chlorophenoxide in diphenyl sulphone at temperatures in excess of 300° C. The rate of reaction is dependent on the reactivity as well as concentration of the reactive species. When compared with the sparse solubility (0.1%) of the bisphenoxide (Polymer, 1981, Vol. 22, page 1096) in its reaction with difluorobenzophenone, the complete solubility of the chlorophenoxide more than compensates for decreased reactivity leading to an overall increased rate of reaction with the chlorophenoxide as compared to difluorobenzophenone and the bisphenoxide.

Though the fluorophenoxide is also completely soluble in diphenylsulphone, branching in the polymer made by this route is observed caused by abstraction of protons ortho to the aromatic fluorine atoms and the generation of carbanions. The same is not possible in the case of the chlorophenoxide due to the much lower electronegativity of chlorine.

The polymerization is preferably carried out in an inert atmosphere e.g. argon or nitrogen.

The reaction vessel is preferably either made from a stainless steel which is not prone to attack at the reaction temperatures in the presence of an alkali metal halide such as sodium chloride, or is made of or lined with titanium, nickel or an alloy thereof, such as Hastelloy C, Hastelloy B, Monel or Inconel. Normal stainless steels such as SS, 304,316 and 316L are not suitable since they undergo severe attack by the alkali metal halide. In fact polymerization in an SS 304/316 reactor leads to crosslinking and gel formation due to metal catalysed side reactions. The corrosion rates of different materials of construction ("MOC") are set out in Table 2 below:

TABLE 2

| S. No | MOC | Corrosion Rate, mmpy |
|---|---|---|
| 1 | SS316 | 2 |
| 2 | Nickel | 0.2 |
| 3 | Inconel | 0.2 |
| 4 | Monel | 0.3 |
| 5 | Hastelloy C | 0.03 |
| 6 | Hastelloy B | 0.03 |
| 7 | Titanium | 0.02 |

The preferred material of construction is Substance No 5, Hastelloy C®.

At the end of the polymerization reaction in order to neutralize the reactive phenoxide end groups, at least one reactive mono functional halide such as methyl chloride or a reactive aromatic halide such as 4-fluorobenzophenone is introduced to end cap the reaction.

As a result of our work we have also found that it is highly desirable to maintain the pH of the polymerization reaction mass in the alkaline range of 9-11. If the pH is maintained in this range the polymerization proceeds smoothly and the subsequent end capping is also efficient. However if the pH drops to below 9, then the polymerization becomes sluggish and the endcapping of the polymer is not efficient with subsequent poor thermal stability of the resultant polymer. To maintain the pH between 9-11 at least one appropriate buffering agent is desirably added. The suitable buffering agent include magnesium oxide and hydroxide, calcium oxide and hydroxide, alkali metal carbonates, calcium carbonate, alkali metal aluminum silicates (sometimes known as zeolites), potassium phosphate and potassium hydrogen phosphate, sodium phosphate and sodium hydrogen phosphate, and the like. Mixtures of buffering agents can also be used. Alkali metal aluminum silicates, potassium phosphate, sodium phosphate, potassium carbonate and sodium carbonate singly or in combination are the preferred buffering agents.

The amount of buffering agent to maintain the pH between 9 and 11 can vary from 0.5-5 mole/weight % and the more preferred range is from 1-3% mole/weight %.

It is also surprisingly found that by the method of the invention described hereunder it is possible to conduct a continuous polymerization of 4-chloro 4'-hydroxy benzophenone. The nucleophilic routes for making PEEK and PEK which are currently commercially practiced use two monomers, the so called AA BB polymerisation reaction between difluorobenzophenone and dihydroxy-benzophenone in the case of PEK and difluorobenzophenone and hydroquinone in the case of PEEK. As is well known to those practised in the art, with a two monomer system, the molecular weight is dependant on the stoichiometric ratio of the two monomers. It is practically impossible to maintain an exact stoichiometry between the two monomers. Hence the dihalobenzenoid compound is added in a slight excess. Maintaining a slight excess of the dihydrobenzenoid compound instead results in poor thermal stability of the resultant polymer. In the AA BB polymerization reaction system the amount of the excess of one reactant over another affects both the rate of the polymerization reaction and the degree of polymerization that is achievable. Due to this limitation it is very difficult to practice a continuous polymerization system with the AA BB polymerisation reaction.

However by the method of polymerization using 4-chloro 4'-hydroxy benzophenone, which is the so called AB type of monomer, the stoichiometric ratio between the halogen and phenolic moieties is inherently exactly equal to one. Hence it is possible both theoretically and practically to maintain a steady reaction rate as well as achieve very large molecular weight buildups. With this possibility it is practically feasible to design and operate a continuous polymerization system.

The present invention will now be explained below in further detail with examples of specific embodiments. However it should be understood that the present invention is by no means restricted to the specific examples given below.

EXAMPLE 1

100 g of crude CHBP were taken for vacuum distillation for further purification to remove non-volatile substances. The apparatus consisted of a flask heated by the heating oil Therminol®, an externally electrically heated vapor line, a solid scraping condenser, and a solids receiver. In an alternative arrangement the vapor line could directly lead to the receiving pot which was kept cooled, and the product could then be removed by melting and casting into a tray.

The crude product was melted in the flask at least 200° C. and then a vacuum was applied to reduce the pressure in the flask to 1-2 mmHg. The distillation occurred in a vapor temperature range of 210-225° C. The distillation took about 1 hr. The distillate weight was 86 g, i.e. 86% recovery, and its purity was found to be 99.5% by glc. It was a white material of high purity. The product was directly used for polymerization.

EXAMPLE 2

100 g of the product obtained in Example 1 were mixed with 260 g of pure diphenyl sulfone in a 1000 ml distillation flask. The mixture was melted and distilled under vacuum directly at a vapor temperature of 192-205° C. at a pressure of 2 mmHg. The product had a lower melting point and boiling range than CHBP itself. The distilled product was analyzed by glc analysis. The analysis indicated that 96 g of CHBP had distilled out along with the $DPSO_2$ solvent. The distillation residue weighed 3.5 g indicating very low degradation during distillation. The distilled product along with the co-distilled $DPSO_2$ was used for polymerization.

EXAMPLE 3

116.3 g of the distilled CHBP obtained from Example 2 was mixed with 300 g of diphenyl sulfone in a polymerization reactor made of Hastelloy C®. The reactor consisted of a 3" dia cylindrical vessel with an oil heating jacket arrangement. The stirrer was of a gate type fabrication. The stirrer motor was provided with a sensor arrangement for measuring the torque developed during the polymerization reaction and to indicate the viscosity level of the reaction mixture. A thermocouple temperature indicator was present in the reactor to measure the reaction mixture temperature. Provision for $N_2$ gas purging of the reactor was also made.

To the reaction mixture, 0.2625 moles of $K_2CO_3$ (36.30 g) passable through a 200 mesh sieve was added at 135° C. The mixture was heated to 200° C. and maintained for one hour under an $N_2$ atmosphere to facilitate the dehydration of the mixture. The temperature was then increased to 250° C. and maintained at this temperature for 1 hour. The temperature was then increased to 300° C. over 1.5 hrs and maintained for 2 hrs. The temperature was then further raised to 330° C. over 1 hr and maintained at this temperature for 3 hours when the required viscosity of the reaction mixture was attained. The pH of the reaction mass was analysed and was found to be 6.7. The polymer was end capped by adding 1 mole % of 4-fluoro benzophenone and maintaining for 0.5 hrs.

The reaction mixture was cooled to 300° C. and discharged into another vessel containing 21 of chlorobenzene solvent kept stirred at 130° C. The mixture was filtered at 130° C. and the cake refluxed with chlorobenzene and filtered. The process was repeated 4 or 5 times until all the $DPSO_2$ solvent was leached out. The cake was further refluxed with water to remove mineral salts and dried to give 93 g of solids—a yield of 95% PEK polymer. The solids as a 0.25% solution in 98% $H_2SO_4$ had an inherent viscosity of 0.92 dl/g. However on extruding the polymer at 400° C., the obtained strands were not very strong, the colour of the strands was also dark, and the polymer had poor thermal stability.

EXAMPLE 4

The experimental procedure of Example 3 was repeated with the exception that the distillate mixture of CHBP and $DPSO_2$ obtained from Example 2 was directly used after analyzing the content of CHBP in it. The batch size was adjusted to 0.5 mole (116.3g) CHBP as in Example 3 and the process was continued in the same way.

The weight of product obtained was 94 g, i.e. a weight yield of 96%. The inherent viscosity measured as a 0.20% solution in 98% $H_2SO_4$ at 25° C. was 0.93 dl/g.

EXAMPLE 5

Into 119 gms of water were added CHBP 244.2 gms (1.05 mols) and 5N NaOH—200 ml (1.0 mols) in 10 lots over 5 hrs while stirring the mass, keeping CHBP in excess until the end. The mass was filtered and the solids on drying amounted to 8.9 gms. The filtrate was analyzed and showed NaCHBP—0.975 mols and CHBP—0.042 mols. After adding an additional 0.0328 mols of NaOH the solution was re-analyzed. It had no free alkali and no free CHBP and the NaCHBP content was 0.97 mols.

The aqueous solution was transferred to a 2 Hastelloy C reactor. To this solution was added 1 mole % of $Na_2CO_3$ and 1 mole % of $Na_3PO_4$ as a buffering agent. Water was distilled off initially at atmospheric pressure and later azeotropically by adding MCB and using Dean and Stark apparatus to remove the last traces of water. After all the water was removed, MCB was distilled off under a nitrogen atmosphere while simultaneously feeding in 800 gm/mole $DPSO_2$ and raising the temperature to 200° C. Then the mass was heated to 250° C. in 0.5 hrs, and pressure was reduced to 100 mm Hg over 45 min, maintained for 1 hr, and the vacuum released with nitrogen. Then the mass was heated to 302° C. over the next 2 hrs and maintained at 300° C. for two hours and then raised to 315° C. and maintained for 3.0 hrs to obtain for the reaction mass an IV of 0.94 dl/g. The reaction mass was endcapped by the addition of methyl chloride and the polymer details are as set out in Table 3 below:

TABLE 3

| Time, Temp profile | pH | Inherent Viscosity dl/g | Mw | Mn | Mw/Mn |
|---|---|---|---|---|---|
| 3 hr at 315° C. | 10.7 | 0.94 | 65000 | 25000 | 2.6 |

On extruding the polymer at 400° C., the obtained strands were very strong, the colour of the strands was light, and the polymer had excellent thermal stability.

EXAMPLE 6

0.98 m/m methanolic NaOH 0.94N was mixed into 500 ml of methanol and 1 mole of CHBP under $N_2$. After the addition of methanolic NaOH were added 0.04 eq. $Na_2CO_3$ solid and 0.01 mole $K_3PO_4$ (as buffering agent) and the reaction mixture was stirred at room temperature for 30 min. Then the methanol was distilled out under $N_2$ to isolate Na—CHBP.

Into a 1 l Hastelloy C® reactor, under an $N_2$ flow of 5 l/hr, there were charged 0.48 moles NaCHBP and $DPSO_2$ 1000 gm/mole. Heating over 3 hrs reached 250° C. and then that temperature was maintained for 2 hrs. After reaching 250° C. the pressure was reduced to 100 mm Hg and maintained for 1 hr. The vacuum was then released with nitrogen and the reaction mass heated to 320° C. in 1.5 hr. After reaching the desired viscosity the reaction mass was endcapped by reaction with methyl chloride. The polymer details are as set out in Table 4 below:

TABLE 4

| Time, Temp profile | pH | Inherent Viscosity dl/g | Mw | Mn | Mw/Mn |
|---|---|---|---|---|---|
| 2 hr at 320° C. | 10.4 | 0.94 | 65000 | 25000 | 2.6 |

On extruding the polymer at 400° C., the obtained strands were very strong, the colour of the strands was light and the polymer had excellent thermal stability.

EXAMPLE 7

0.95 m/m methanolic KOH 1.0036N was mixed into a solution of 1 mole of CHBP in 500 ml of methanol under an $N_2$ atmosphere. Then 0.07 eq. of $K_2CO_3$ solid and 2.4 gm of Zeolite MS 4A (as buffering agent) were added and the reaction mixture stirred at room temperature for 30 min. Then the methanol was distilled off under $N_2$ to isolate K—CHBP.

Into a 1 l Hastelloy CR® reactor, under an $N_2$ flow of 5 l/hr, there was charged 0.35 moles K—CHBP and 1000 gms/mole of $DPSO_2$. Heating over in 3 hrs reached 250° C. and then that temperature was maintained for 2 hrs. After reaching 250° C. the pressure was reduced to 100 mm Hg and maintained for 1 hr. The vacuum was then released with nitrogen and the reaction mass heated to 305° C. in 1 hr. After reaching the desired viscosity the reaction mass was endcapped by reaction with methyl chloride. The polymer details are as set out in Table 5, below:

TABLE 5

| Time, Temp profile | pH | Inherent Viscosity dl/g | Mw | Mn | Mw/Mn |
|---|---|---|---|---|---|
| 2 hr at 305° C. | 10.4 | 1.10 | 77560 | 27700 | 2.80 |
| 4 hr at 305° C. | 10.0 | 1.35 | 93500 | 31100 | 3.00 |

On extruding the polymer at 400° C., the obtained strands were not strong, the colour of the strands was dark, and the polymer did not have good thermal stability.

EXAMPLE 8

CHBP 540 gm (2.3217 moles) was changed into 500 ml methanol. To this slurry were added 1.500 l of 1.4704 N methanolic NaOH 2.2056 (moles) corresponding to 0.95 m/m, at room temperature over 30 min. The slurry was rinsed with 200 ml methanol and stirred at room temperature for 15 min. Then $Na_2CO_3$ 9.5 gm was added corresponding to 0.09 eq/mole along with $Na_3PO_4$ 4.9 gm as a buffering agent corresponding to 3 mole %. From the solution methanol was distilled off under $N_2$ to isolate NaCHBP 1000 gms of $DPSO_2$ were charged into a 5 l Hastelloy C® reactor, together with 509.2 gm of NaCHBP corresponding to 2 moles. Then were added 1000 gm of $DPSO_2$ and the reaction mass was heated to 150° C. in 1.75 hrs, heated further to 250° C. in 1.25 hrs and then maintained at 250° C. for 2 hrs. After reaching 250° C. the pressure was reduced to 100 mm Hg and maintained for 1 hr. The vacuum was then released with nitrogen and the reaction mass were heated to 305° C. in 1 hr, heated to 315-320° C. in 2.25 hr and maintained at 315-320° C. After the required viscosity was obtained, the reaction mass were endcapped with methyl chloride. The polymer details are as set out in Table 6 below:

TABLE 6

| Time, Temp profile | pH | Inherent Viscosity dl/g | Mw | Mn | Mw/Mn |
|---|---|---|---|---|---|
| 1 hr at 315-320° C. | 10.1 | 1.04 | 67600 | 26000 | 2.60 |
| After endcapping at 315-320° C. | 9.6 | 1.11 | 72900 | 27000 | 2.70 |

On extruding the polymer at 400° C., the obtained strands were very strong, the colour of the strands was light and the polymer had excellent thermal stability.

EXAMPLE 9

Into a 5 l Hastelloy C® reactor under a nitrogen atmosphere were charged 1000 gms of DPSO$_2$, 465 gms of distilled CHBP, 106 gms of Na$_2$CO$_3$ and 2.76 gms of K$_2$CO$_3$ as buffering agent. The whole mass was slowly heated to 100° C. with stirring when this was possible. After this the temperature was slowly raised to 150° C. over 4 hours. Subsequently the temperature was raised to 250° C. over 2 hours and maintained for 2 hours. After reaching 250° C. the pressure was reduced to 100 mm Hg and maintained for 1 hr. The vacuum was released with nitrogen and then the reaction mass heated to 305° C. in 1 hr, maintained at 300° C. for 2 hours and then raised to 320° C. over 2 hours. The polymer details are as set out in Table 7 below:

TABLE 7

| Time, Temp profile | pH | Inherent Viscosity dl/g | Mw | Mn | Mw/Mn |
|---|---|---|---|---|---|
| 1.5 hr at 315-320° C. | 10.2 | 0.83 | 52800 | 22000 | 2.4 |
| After endcapping at 315-320° C. | 9.6 | 1.02 | 65000 | 25000 | 2.6 |

On extruding the polymer at 400° C., the obtained strands were very strong, the colour of the strands was light and the polymer had excellent thermal stability.

EXAMPLE 10

To a slurry of molten DPSO$_2$ (400 gms) with Na$_2$CO$_3$ (108.12 gm) and Na$_3$PO$_4$ (3.28 gm) in a 5 l Hastelloy C® reactor under an N$_2$ atmosphere, were slowly added a mixture of DPSO$_2$ (700 gm) and distilled CHBP (465.2 gm) from a 5 l SS 316 feeding reactor at 160° C. over 1 hour under agitation. 100 gm DPSO$_2$ was used for rinsing the feeding reactor.

The reaction mass was maintained at 160° C. for 2 hrs, heated to 200° C. in 1 hr, maintained at 200° C. for 1 hr, and then further heated to 250° C. in 1.5 hr. The pressure was reduced slowly over 1 hr to 100 mm Hg and maintained for 1 hr at 250° C. The vacuum was then released with N$_2$ and the reaction mass heated to 315° C. in 2 hr. The polymer details are as set out in Table 8 below:

TABLE 8

| Time, Temp profile | pH | Inherent Viscosity dl/g | Mw | Mn | Mw/Mn |
|---|---|---|---|---|---|
| 1.0 hr at 315-320° C. | 10.3 | 0.82 | 53000 | 22000 | 2.4 |
| After endcapping at 315-320° C. | 9.6 | 0.94 | 62000 | 25000 | 2.5 |

On extruding the polymer at 400° C., the obtained strands were very strong and the colour of the strands was light, and the polymer had excellent thermal stability.

EXAMPLE 11

0.98 m/m of methanolic NaOH 0.94N were added into 500 ml of methanol and 1 mole of CHBP under N$_2$. Then were added 0.04 eq of Na$_2$CO$_3$ solid and the reaction mass was stirred at room temperature for 30 min. The methanol was distilled off under N$_2$ to isolate Na—CHBP.

This was charged into 210 gms of DPSO$_2$ into a 1 l Hastelloy C® reactor and then O$_2$ content within the reactor reduced to 0% by purging with N$_2$. The reactor mass was heated to 150° C. with stirring, and then heated to 315° C. in 1 hr. A mixture of 0.483 gm of K$_2$CO$_3$ and 89.1 gm (0.35 moles) of dry Na—CHBP were added together and the reaction mass maintained for 1 hr. Thereafter a sample was removed and analysed for inh.V. The polymer details are as set out in Table 9 below:

TABLE 9

| Time, Temp profile | pH | Inherent Viscosity dl/g | Mw | Mn | Mw/Mn |
|---|---|---|---|---|---|
| 1.0 hr at 315° C. | 10.3 | 1.05 | 167600 | 26000 | 2.6 |

On extruding the polymer at 400° C., the obtained strands were very strong and the colour of the strands was light and the polymer had excellent thermal stability.

EXAMPLE 12

Continuous Polymerization System

A continuous polymerization system was set up consisting of two 5 l Hastelloy C® continuously stirred tubular reactors, arranged in series, followed by a filtration system consisting of nickel filters having a 200 mesh size, followed by an extrusion apparatus.

Into the first Hastelloy C® reactor held at 310° C. under a nitrogen atmosphere at a pressure of 5 Kg/cm$^2$ with agitation was fed in through a screw mixer, a solid heated mixture of 891 gms/hr of dry NaCHBP and 9 gms/hr of Zeolite MS4A as buffering agent. Simultaneously there was fed in to this reactor 2100 gms/hr of DPSO$_2$ heated to 330° C. After undergoing polymerization in the first reactor, the polymerization reaction mass was fed into the second reactor at a rate of 3000 gm/hr at a temperature of 315° C. Into the second polymerization reactor held at 4 Kg/cm$^2$ by pressure of methyl chloride gas was simultaneously fed in 1400 gms/hr of Molten DPSO$_2$ heated to 315° C. From the second reactor, 4400 gms/hr of endcapped reaction mass is passed through the filtration system to remove NaCl. The filtered reaction mass was then passed through a specially designed extruder at 400° C. where the solvent diphenyl sulphone was distilled off under vacuum and 680 gms/hr of polymer PEK pellets was obtained as the extrudate. This extrudate PEK possessed a high molecular weight and good thermal stability, as well as very good mechanical properties.

What is claimed is:
1. A process for the production of purified 4-chloro-4'-hydroxy benzophenone comprising distilling under reduced pressure a liquid containing 4-chloro-4'-hydroxy benzophenone and a compatible solvent which lowers the boiling point of the 4-chloro-4'-hydroxy benzophenone and is thermally stable at the lowered boiling point.

2. A process as claimed in claim 1, wherein the compatible solvent is diphenyl sulphone.

3. A process as claimed in claim 1 wherein the compatible solvent is benzophenone.

4. A process as claimed in claim 1 where the distillation pressure is less than 5 mmHg.

5. A process as claimed in claim 2 wherein the ratio in the liquid being distilled of 4-chloro-4'hydroxybenzophenone to diphenyl sulphone is between 1:2 and 1:5 by volume.

6. A process as claimed in claim 2 wherein the ratio in the liquid being distilled of 4-chloro-4'hydroxybenzophenone to diphenyl sulphone is 1:2.6 by volume.

7. A process for the preparation of alkali metal salt of 4-chloro-4'-hydroxy benzophenone comprising the steps of (a) preparing purified 4-chloro-4'-hydroxy benzophenone by a process comprising distilling under reduced pressure a liquid containing 4-chloro-4'-hydroxy benzophenone and a compatible solvent which lowers the boiling point of the 4-chloro-4'-hydroxy benzophenone and is thermally stable at the lowered boiling point, and then (b) preparing the alkali metal salt of the purified 4-chloro-4'-hydroxy benzophenone by the reaction of the purified 4-chloro-4'-hydroxy benzophenone with a stoichiometric excess of at least one alkali metal base, wherein the at least one alkali metal base is selected from the group consisting of sodium hydroxide, sodium carbonate, and sodium bicarbonate.

8. A process as claimed in claim 7 wherein the alkali metal salt of the purified benzophenone is prepared by the reaction of the purified 4-chloro-4'-hydroxy benzophenone with a stoichiometric excess of a combination of two bases.

9. A process as claimed in claim 8 where a combination of two bases is used and sodium carbonate or sodium bicarbonate is used to provide the excess of base when sodium hydroxide has been pre-reacted in a stoichiometric proportion or stoichiometric deficiency with the purified 4-chloro-4'-hydroxy benzophenone.

10. A process as claimed in claim 8 where a combination of two bases is used and sodium carbonate is used to provide the excess of base when sodium hydroxide has been pre-reacted in a stoichiometric proportion or stoichiometric deficiency with purified 4-chloro-4'-hydroxy benzophenone.

11. A process as claimed in claim 7, including the step of dehydrating the alkali metal salt by the application of a vacuum, by spray drying of the aqueous solution or by azeotropic distillation using a chlorinated aromatic solvent.

12. A process for the polymerization of alkali metal salt of 4-chloro-4'-hydroxy benzophenone comprising the steps of (a) preparing purified 4-chloro-4'-hydroxy benzophenone by a process comprising distilling under reduced pressure a liquid containing 4-chloro-4'-hydroxy benzophenone and a compatible solvent which lowers the boiling point of the 4-chloro-4'-hydroxy benzophenone, and (b) preparing the alkali metal salt of the purified 4-chloro-4'-hydroxy benzophenone by the reaction of the purified 4-chloro-4'-hydroxy benzophenone with a stoichiometric excess of at least one alkali metal base, and (c) polymerizing the alkali metal salt of the purified 4-chloro-4'-hydroxy benzophenone under conditions controlled to produce polyether ketone (PEK) having an inherent viscosity >0.9 dl/g.

13. A process as claimed in claim 12 where the polymerization may be conducted either in batch, semi-batch or continuous mode of operation.

14. A process as claimed in claim 12 wherein the alkali metal salt of the purified benzophenone is polymerized in the presence of diphenyl sulphone.

15. A process as claimed in claim 12 wherein the alkali metal salt of the purified benzophenone is polymerized in the presence of benzophenone.

16. A process as claimed in claim 12 where before the polymerization temperature is reached a partial vacuum of 25 to 400 torr is applied at temperature above 150° C. to eliminate traces of moisture remaining in the alkali metal salt.

17. A process as claimed in claim 12 wherein the polymerization is carried out at temperature of 305-320° C.

18. A process as claimed in claim 12 wherein a buffering agent is added to maintain the pH of the reaction mass between 9 and 11.

19. A process as claimed in claim 18 wherein the buffering agent is selected from the group consisting of magnesium oxide, magnesium, hydroxide, calcium oxide, calcium hydroxide, alkali metal carbonates, calcium carbonate, alkali metal aluminum silicates, zeolites, potassium phosphate, potassium hydrogen phosphate, sodium phosphate and sodium hydrogen phosphate.

20. A process as claimed in claim 18 wherein the total amount of buffering agent is from 0.5-5 mole/weight%.

21. A process as claimed in claim 18 wherein the total amount of buffering agent is from 1-3 mole/weight%.

22. A process as claimed in claim 18 wherein the buffering agent is selected from the group consisting of alkali metal aluminum silicates, potassium phosphate, sodium phosphate, potassium carbonate, and sodium carbonate, singly or in combination.

23. A process as claimed in claim 12 wherein the at least one base is selected from the group consisting of sodium hydroxide, sodium carbonate, and sodium bicarbonate.

* * * * *